United States Patent [19]
Grill

[11] Patent Number: 5,630,943
[45] Date of Patent: May 20, 1997

[54] DISCONTINUOUS COUNTERCURRENT CHROMATOGRAPHIC PROCESS AND APPARATUS

[75] Inventor: Charles M. Grill, East Greenwich, R.I.

[73] Assignee: Merck Patent Gesellschaft Mit Beschrankter Haftung, Darmstadt, Germany

[21] Appl. No.: 566,425

[22] Filed: Nov. 30, 1995

[51] Int. Cl.$^6$ ............................................ B01D 15/08
[52] U.S. Cl. .................. 210/659; 210/656; 210/198.2
[58] Field of Search ................................. 210/635, 656, 210/659, 198.2

[56] References Cited

U.S. PATENT DOCUMENTS

| | | | |
|---|---|---|---|
| 3,992,175 | 11/1976 | Klementi et al. | 55/67 |
| 4,001,112 | 1/1977 | Barker et al. | 210/31 C |
| 4,267,054 | 5/1981 | Yoritomi et al. | 210/659 |
| 4,359,323 | 11/1982 | LePage | 23/230 M |
| 4,379,751 | 4/1983 | Yoritomi et al. | 210/659 |
| 4,412,866 | 11/1983 | Schoenrock et al. | 127/46.2 |
| 4,478,720 | 10/1984 | Perrut | 210/659 |
| 4,498,991 | 2/1985 | Oroskar | 210/659 |
| 4,528,101 | 7/1985 | Burke et al. | 210/656 |
| 4,530,234 | 7/1985 | Cullick et al. | 73/53 |
| 4,536,199 | 8/1985 | Toon | 55/67 |
| 4,840,730 | 6/1989 | Saxena | 210/198.2 |
| 4,919,595 | 4/1990 | Likuski et al. | 417/18 |
| 4,970,002 | 11/1990 | Ando et al. | 210/659 |
| 4,990,259 | 2/1991 | Kearney | 210/659 |
| 5,064,539 | 11/1991 | Tanimura | 210/659 |
| 5,071,547 | 12/1991 | Cazer et al. | 210/198.2 |
| 5,089,126 | 2/1992 | Silebi et al. | 210/198.2 |
| 5,093,004 | 3/1992 | Hotier et al. | 210/659 |
| 5,100,557 | 3/1992 | Nogami et al. | 210/656 |
| 5,108,466 | 4/1992 | Klein et al. | 55/20 |
| 5,114,590 | 5/1992 | Hotier et al. | 219/659 |
| 5,122,275 | 6/1992 | Rasche | 210/198.2 |
| 5,166,076 | 11/1992 | Müller et al. | 436/161 |
| 5,180,487 | 1/1993 | Saito et al. | 210/198.2 |
| 5,196,039 | 3/1993 | Phillips et al. | 55/67 |
| 5,253,981 | 10/1993 | Yang et al. | 417/3 |
| 5,384,035 | 1/1995 | Smolnik et al. | 210/635 |
| 5,393,420 | 2/1995 | Hutchins et al. | 210/198.2 |
| 5,393,434 | 2/1995 | Hutchins et al. | 210/656 |
| 5,398,539 | 3/1995 | Gordon et al. | 73/23.35 |

FOREIGN PATENT DOCUMENTS 0127926  12/1984  European Pat. Off. ............ 210/198.2

OTHER PUBLICATIONS

Henry et al., "High Speed Recycle Chromatography Using an Alternate . . . ", J. of Chromatographic Science, vol. 12, pp. 197–199, Apr. 1974.

Broughton et al., "The Parex Process For Recovering Paraxylene", Chem. Eng. Progress, 66(9): 70–75, Sep. 1970.

*Primary Examiner*—Ernest G. Therkorn
*Attorney, Agent, or Firm*—Millen, White, Zelano & Branigan, P.C.

[57] ABSTRACT

A preparative chromatographic cyclical process comprising, at steady state: establishing a figure-of-eight circulating chromatographic profile between two chromatographic columns with the provision that said chromatographic profile never passes through a pump; discontinuously and periodically injecting a sample comprising at least two components, into said circulating profile; and collecting, discontinuously and periodically, at least two enriched fractions from said circulating profile, the apparatus for conducting this process comprising only two chromatographic columns, at least one solvent pump, an injection pump, two 4-way valves, and conduit communicating said columns and the two 4-way valves in the form of a figure-of-eight pattern without traversing a pump, and conduit communicating said at least one solvent pump and at least one of said columns.

9 Claims, 17 Drawing Sheets

DISCONTINUOUS COUNTERCURRENT CHROMATOGRAPHIC PROCESS AND APPARATUS

FIELD OF THE INVENTION

The invention relates to processes of performing preparative chromatography in an efficient, repetitive manner, as well as to apparatus therefor.

BACKGROUND OF THE INVENTION

Among the numerous proposed and utilized chromatographic techniques are: (1) high performance liquid chromatography (HPLC) with external recycling and (2) simulated moving bed (SMB) chromatography. External HPLC recycling has been known since at least 1974 (R. A. Henry, S. H. Byrne, and D. R. Hudson, *J. Chromatographic Sci.* 12, 197 (1974)). In external recycling, the chromatographic peaks are caused to cycle through two columns in a figure-of-eight pattern so as to increase the number of theoretical plates. During the recycling procedure, the peaks do not pass through a pump. Thus, this technique is more efficient than closed loop recycling in which the peaks pass through a pump each cycle, causing mixing and cancellation of some of the separation that occurs in the column.

SMB chromatography, invented in the early 1960's by workers at UOP (D. B. Broughton, R. W. Neuzil, J. M. Pharis, C. S. Brearley, *Chem. Eng. Progress,* 66(9), 70 (1970)), is a continuous process. Feed is continuously injected into the interior of the SMB profile; extract and raffinate are continuously collected; and fresh mobile phase is also added continuously. The entire profile travels around the system. For example, in one possible configuration of a 16 column array, the feed is injected between columns 7 and 8; the mobile phase is injected between columns 16 and 1; the raffinate is collected between columns 11 and 12; and the extract is collected between columns 3 and 4. As the profile moves to the right, all the injection and collection points are switched simultaneously one column to the right. For example, the feed point is between columns 9 and 10; the mobile phase point, between columns 1 and 2; the raffinate point between columns 12 and 13; and the extract point, between columns 4 and 5. The switching occurs periodically at the appropriate times. Because the fluids injected through the feed and mobile phases points are collected at the raffinate and extract points, a steady state develops. A further characteristic of SMB chromatography is that there are four flow rates across the profile. It is also important to stress that classical SMB chromatography is truly continuous: the mobile phase and feed pumps never stop pumping material into the system; and the extract and raffinate lines never stop delivering collected purified material.

The prior art also contains three patents that are relevant: U.S. Pat. No. 4,267,054, U.S. Pat. No. 4,379,751, and U.S. Pat. No. 4,970,002. However, the processes of these patents use closed-loop recycling.

SUMMARY OF THE INVENTION

An object of the invention is to provide economical and efficient HPLC processes. Another object is to provide apparatuses for such processes.

Upon further study, of the specification and appended claims, further objects and advantages of this invention will become apparent to those skilled in the art.

To achieve those objects, one aspect of the invention is to employ recycling techniques coupled with the periodic injection of fresh samples.

Another aspect of the current invention resides in the use of a second solvent pump (referred to as Pump 2 in the attached figures) that prevents the chromatographic profile from stalling during the collection of certain fractions. This feature greatly increases the productivity of the process. Thus, the employment of two pumps for two columns is itself a novel and useful subcombination.

In a preferred modification of the invention, a detector is employed, although a detector is not essential for the performance of the invention. By virtue of the preferred use of the detector, the entire process becomes visual and intuitive, greatly facilitating methods development. More importantly, the detector allows the use of software in the initiation of all collection and control events such as the collection of fractions, the injection of fresh sample, column switching, pump control, etc. By measuring parameters such as the ascending or descending slope, characteristic absorbance, ratio of two absorbances, functions of absorbances, refractive index, conductance, pH, characteristic optical activity, etc., such software determines the correct point on the chromatographic profile to initiate a given event. The software also permits collection and control events to be timed events. For example, the detection of the ascending slope coupled with a timer leads to a very satisfactory process.

According to another aspect of the invention the mobile phase pump can be switched off during injection. This prevents the mixing of the fresh sample with the partially separated profile and results in a significantly improved separation. This technique is particularly useful in difficult separations. Of course, where appropriate, the mobile phase pump can be left on during injection.

In another aspect of the invention, a mechanism is provided to generate a pulse of strong solvent to elute later eluting fractions more quickly and to concentrate these fractions.

To perform the process of the invention, features of the apparatus comprise: two preparative chromatographic columns, two 4-way valves used for column switching, at least one and preferably two solvent pumps (Pumps 1 and 2), an injection pump (or system), and a preferably 3-way recycle valve used to send the mobile phase to waste or to recycle it to Pump 1. Any type of preparative chromatographic column can be used. Each column is preferably packed with the same type and amount of stationary phase or an equivalent thereof. For best results, the columns should have nearly the same efficiency as measured by the number of theoretical plates.

It is also preferable to provide a detector, a computer and automation software. It is preferred that some, if not all, control events including, but not limited to, valve switching, toggling on and off of pumps, and adjusting pump flow rates, are initiated by the software solely on the basis of time. Conversely, where no detector is used, it is preferred that the progress and success of the separation is determined by periodic and/or on-line sampling of fractions followed by analysis of the fractions by analytical instruments not associated with the preparative chromatographic process.

The process can be used to perform any type of chromatographic separation including, but not limited to, normal phase chromatographic separations, reverse phase chromatographic separations, chiral chromatographic separations, ion exchange chromatographic separations, affinity chromatographic separations, and size exclusion chromatographic separations.

BRIEF DESCRIPTION OF THE DRAWINGS

For a better understanding of the present invention, a detailed description of the method of chromatographic separation of fluid mixtures into fractions and Examples illustrating the chromatograph embodiments are given with reference to the accompanying drawings, wherein.

DETAILED DESCRIPTION OF DRAWINGS

Figure 1:
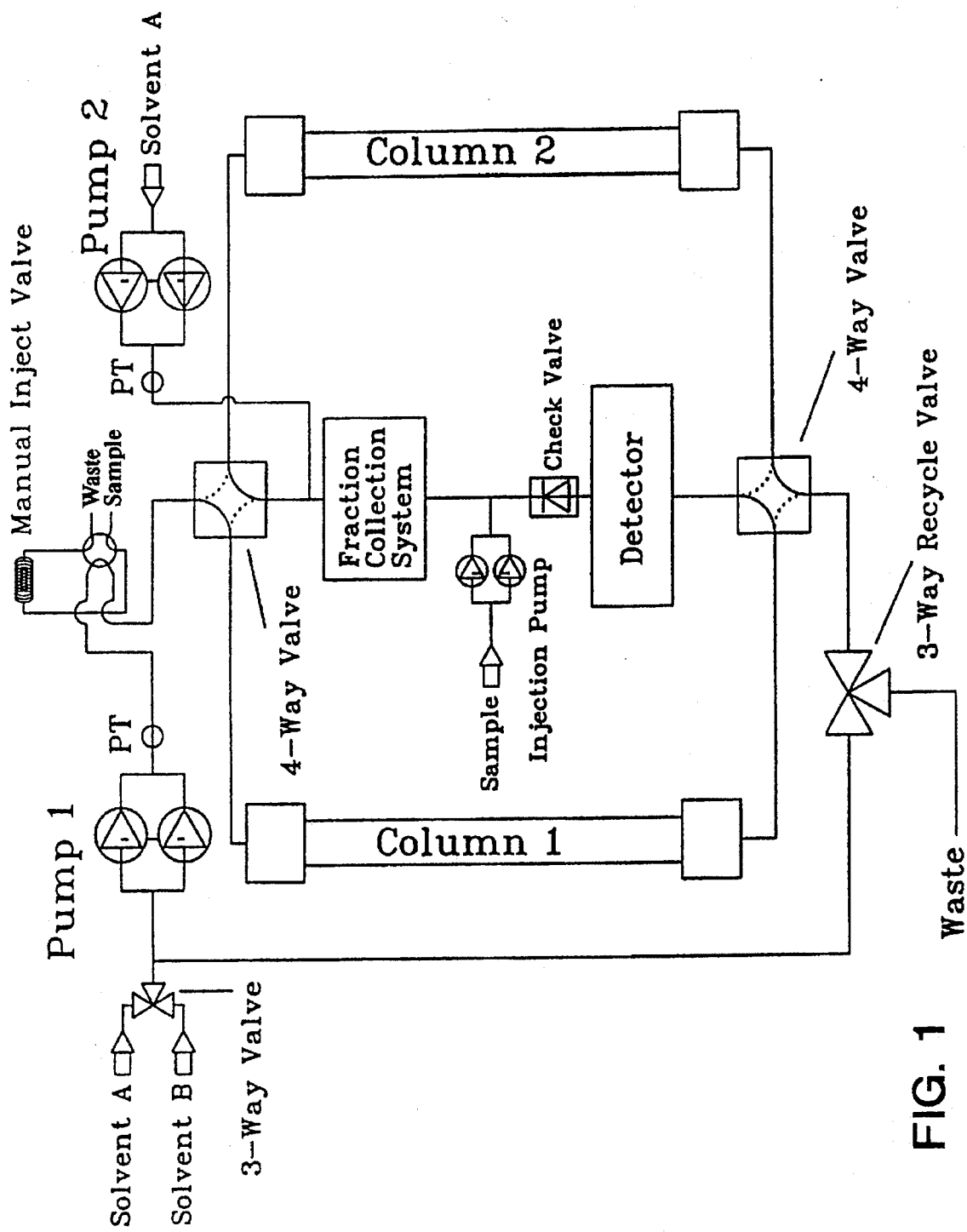
FIG. 1 is a generalized schematic flowsheet of the invention.

At the outset, the abbreviation "PT" in FIG. 1 and in other figures stands for "pressured transducer". The abbreviations "P1 . . . P5" stand for a valve setting permitting air to be introduced and the abbreviations "V1 . . . V5" stand for a valve setting for collecting the fraction.

FIG. 1 shows a generalized schematic diagram of the invention. Virtually any type of fraction collection system used in preparative chromatography can be used to collect purified product. Methods of automated sample injection other than the simple injection pump shown are also possible. The two 4-way valves serve to switch the profile onto the appropriate column. They will switch simultaneously. This event will be a timed event.

Pumps 1 and 2 are mobile phase pumps. The flow rate of Pump 1 is entered into the program at the beginning of the run. Pump 1 can be switched off during injection. This is useful because it prevents mixing of the fresh sample with the partially separated profile, thus resulting in a better separation. This switching off of Pump 1 during injection could be a timed event, or it could be triggered by the relevant parameters determined by the system and software.

Note that Pump 1 can pump either solvent A or solvent B. Solvent A is the separating solvent and is the mobile phase that has been determined to give the best separation. Solvent B is a stronger solvent, e.g., 100% methanol as compared to an 80:20 by volume methanol:water solution. A short pulse of solvent B, can be used to wash the more retained components off the relevant column to be collected by the fraction collection system or rejected to waste. (By "pulse" is meant a momentary injection of solvent B, lasting about 1–10% of the time of complete cycle for example.) This pulse of stronger solvent reduces the time needed to collect these fractions and also significantly increases the concentration of these fractions. After the desired volume of Solvent B has been pumped onto the relevant column, solvent A is again selected for Pump 1. By the time the profile is switched onto this column, the column has been equilibrated with solvent A. The switching between solvents A and B could be a timed event, or it could be triggered by the relevant parameters determined by the system and software.

During the collection of fractions that occur after the injection of fresh portions of the sample, the profile is stalled. The purpose of Pump 2 is to prevent the stalling of the profile. Pump 2 can be turned on during these collection events, causing the profile to continue through the column. Throughput (amount of product collected per unit time) is significantly increased by using Pump 2 to prevent stalling of the profile.

The 3-way recycle valve is typically set to recycle mobile phase to the inlet side of Pump 1 during the operation of Pump 2. This significantly minimizes the amount of mobile phase used, since otherwise the mobile phase from Pump 2 would go to waste. To prevent the solvent A generated by Pump 2 from contaminating the Solvent A reservoir of Pump 1, Pump 2 is run at a slightly lower flow rate than Pump 1. Pump 1 makes up the extra amount of solvent A it needs by drawing it directly from the reservoir.

The 3-way recycle valve can also be set to recycle pure mobile phase to the inlet side of Pump 1 when Pump 2 is shut off and no fractions are being collected. The columns are then connected in series, and Pump 1 provides the entire impetus to move the profile through the columns. Mobile phase leaving the second column in series can be diverted to waste or recycled to the inlet of Pump 1.

The 3-way recycle valve is set to waste during injection. This assures that the system will not be "dead headed" during injection.

The current invention is a repetitive process that can run for hours or days on end. It is, therefore, necessary that it be automated via computer control. TurboPrep® control software, proprietary software of EM Separations Technology, was used in all runs discussed in the examples.

Figure 2:
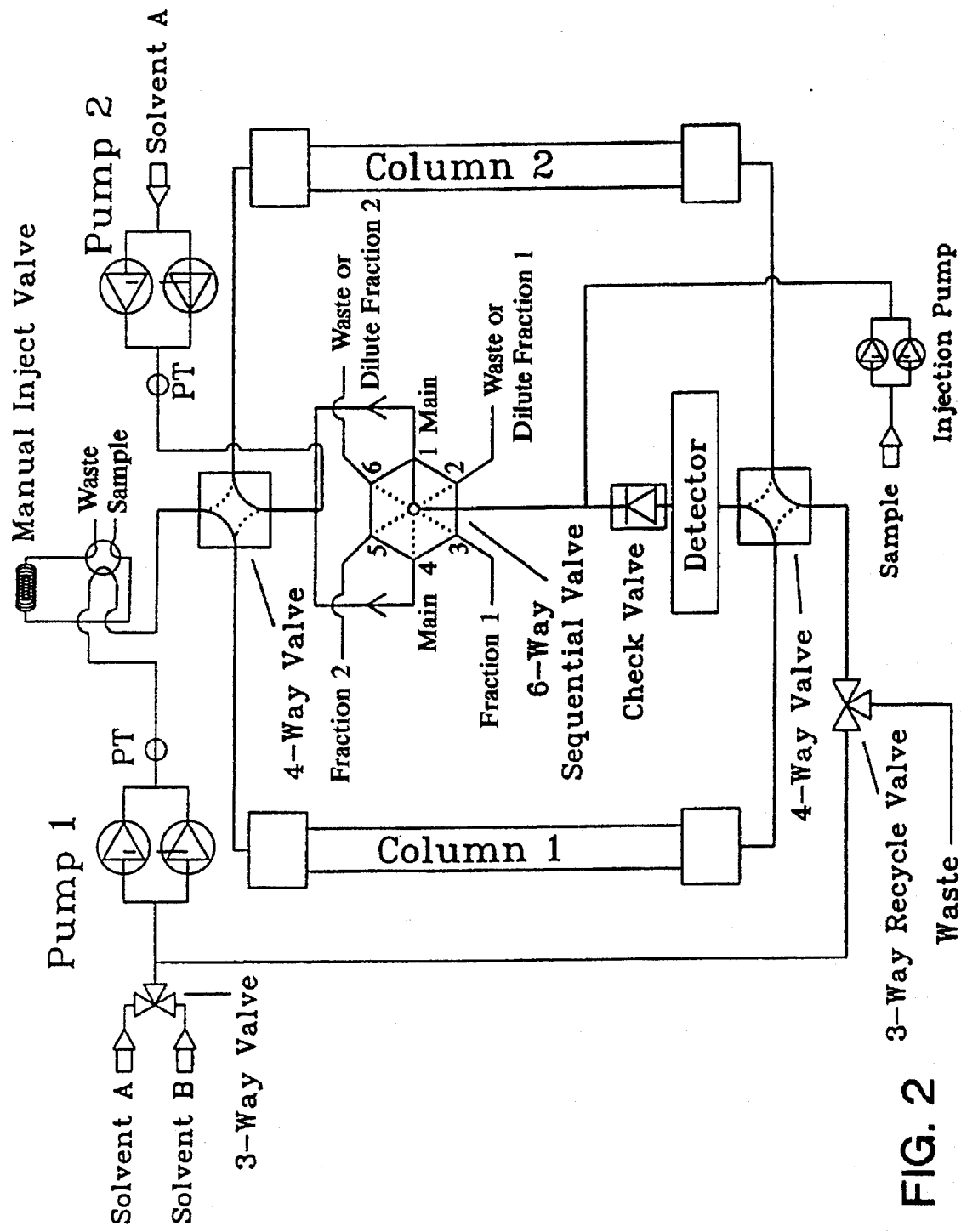
FIG. 2 is another flowsheet of the invention differing from FIG. 1 by the use of a 6-way sequential valve.

FIG. 2 shows one of the preferred embodiments of the current invention in which the collection system is a 6-way sequential valve. This embodiment was used to obtain all the results presented in Examples 1–4. Other preferred embodiments using different fraction collection systems and different injection systems are discussed hereinafter.

The following is a description of the operation of the preferred embodiment shown in FIG. 2. The operation of all embodiments is basically the same, regardless of the fraction collection system or injection system used.

Using the preferred embodiment shown in FIG. 2, the following sequence of events will occur when steady state is reached:

1. The 4-way valves are switched, directing the profile onto the appropriate column. (The 6-way valve is already in position 1.) The recycle valve can be set to recycle mobile phase to the inlet of Pump 1 or to send the stream to waste.

2. The 6-way valve is switched to position 2 to divert the stream to waste in anticipation of the approach of the profile.

3. The 6-way valve is switched to position 3 to collect fraction 1.

4. The 6-way valve is switched to position 4. This stops the collection of fraction 1 and forces the profile to proceed to the next column. The two columns are now connected in series, and Pump 1 provides the entire impetus to move the profile through the 2-column system. The recycle valve is either set to recycle mobile phase to the inlet of Pump 1 or to send the stream to waste.

5. The injection pump is turned on to pump fresh sample into the interior of the profile. During injection the 3-way recycle valve is switched to waste. This assures that the system will not be "dead headed" during injection. Also during injection, Pump 1 may be turned off if desired.

6. The injection pump is turned off. If Pump 1 had been turned off during injection, it will restart when the injection pump is turned off. The recycle valve can be set to recycle mobile phase to the inlet of Pump 1 or to send the stream to waste.

7. The 6-way valve is switched to position 5 to collect fraction 2. During this time, Pump 2 can also be turned on to prevent stalling of the profile.

8. The 6-way valve is switched to position 6. This stops the collection of fraction 2 and diverts the stream to waste to prevent the circulation of uncollected product and contaminants. During this time, Pump 2 can also be turned on to prevent stalling of the profile.

9. The 6-way valve is switched to position 1, and Pump 2 is turned off. The two columns are now connected in series, and Pump 1 provides the entire impetus to move the profile through the 2-column system. The recycle valve can be set to recycle mobile phase to the inlet of Pump 1 or to send the stream to waste.

In the current invention all valve switching occurs sequentially, not simultaneously as in SMB. At steady state the time between the same event in succeeding cycles will be constant and is called the cycle time.

For example, assume the cycle time is 7 minutes. In a certain cycle, say cycle 20, the 4-way valves will switch at a certain time. Seven minutes later, the 4-way valves will switch again to begin the next cycle; seven minutes later, they will switch again; etc. Likewise, at a later time in cycle 20, position 2 on the 6-way valve will be selected; 7 minutes later, position 2 will be selected again; etc. This happens for all the events in each cycle. They all occur again and again, the interval between the same occurrence equaling the cycle time.

Referring to FIGS. 1 and 2, the manual inject valve is not an essential feature of the current invention. Its purpose is to allow testing of the columns by injecting small amounts of standard solutions.

FIGS. 3 through 11 will be discussed in detail in connection with the following Examples.

Figure 12:
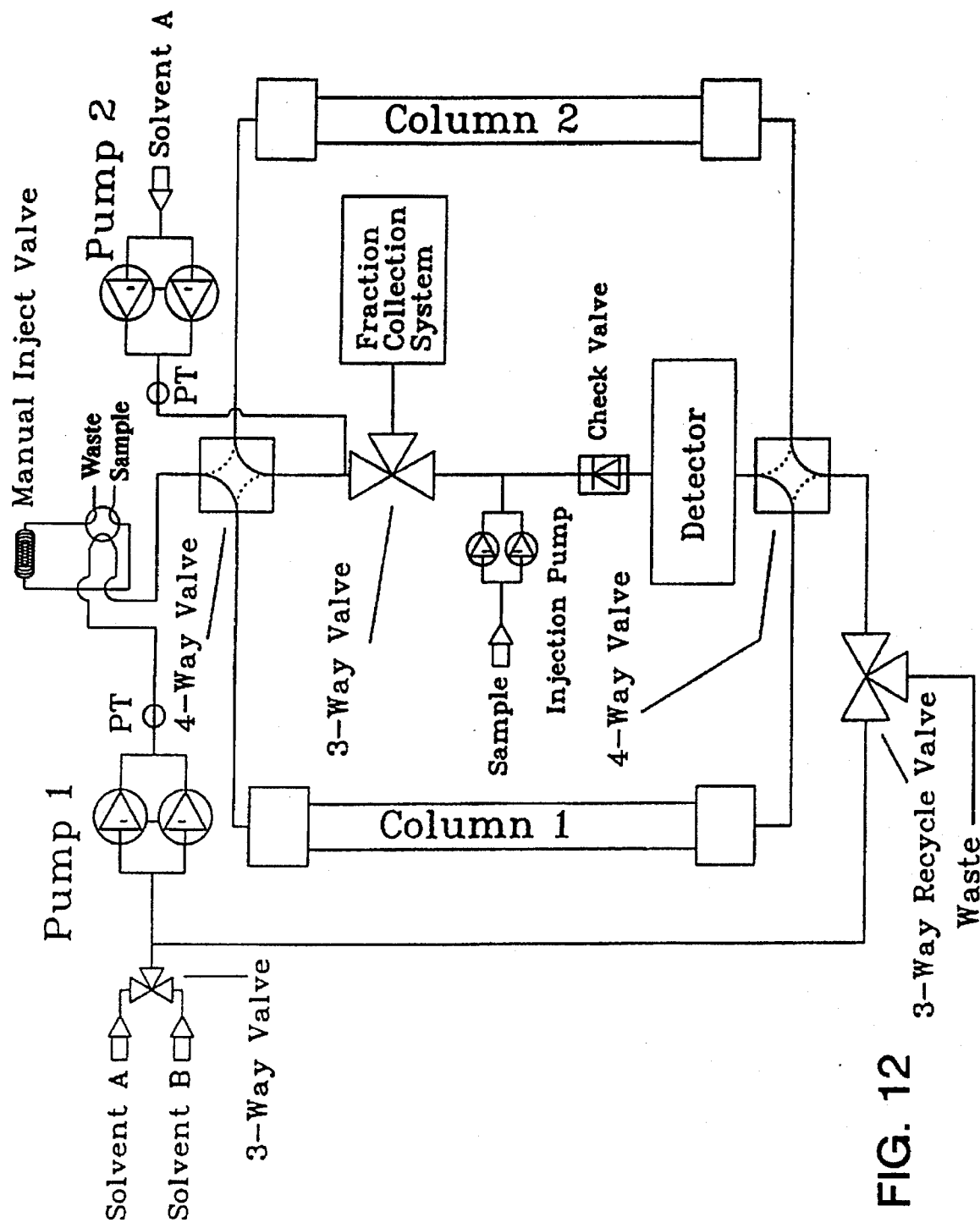
FIG. 12 is a schematic flowsheet of the invention, similar to FIG. 1, but depicting a 3-way valve and a generalized fraction collection system.

FIG. 12 shows a generalized schematic of a fraction collection system that is connected to the rest of the system via a high pressure 3-way valve. Any type of fraction collection system used in preparative chromatography can be connected in this way. One example is a sequential fraction collector in which the tubing conducting the fraction is sequentially interfaced with each fraction collection vessel. Another example is an array of valves connected to a central low dead-volume cavity into which the fraction is conducted; any of the valves can be chosen in any order to conduct the fraction further to the collection vessel of choice.

Figure 13:
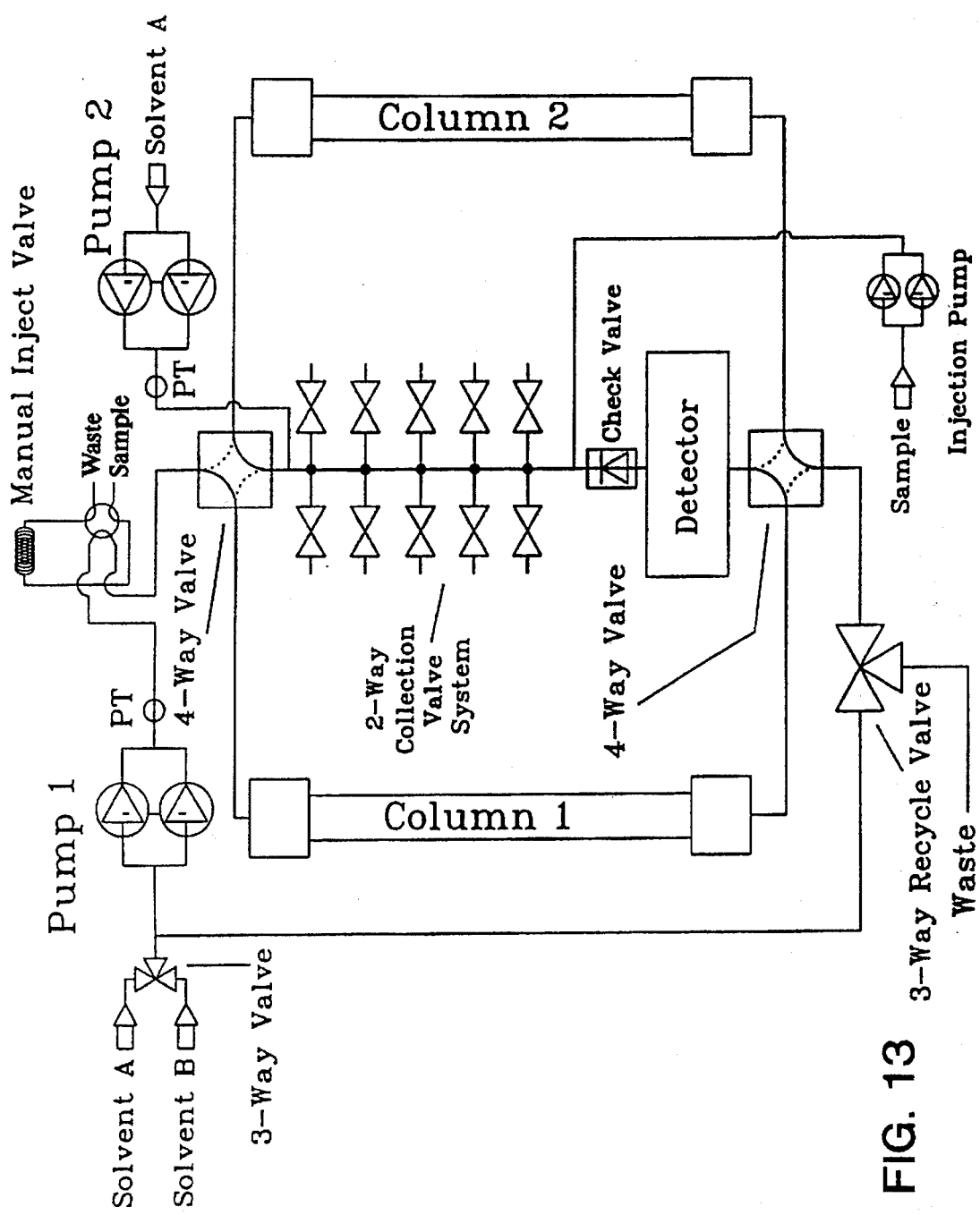
FIG. 13 is similar to FIG. 1, but wherein the fraction collection system is a 2-way collection valve system.

FIG. 13 shows another method of collecting fractions in which a linear array of high pressure 2-way valves is connected to the system via a series of closely spaced cross-shaped fittings.

Figure 14:
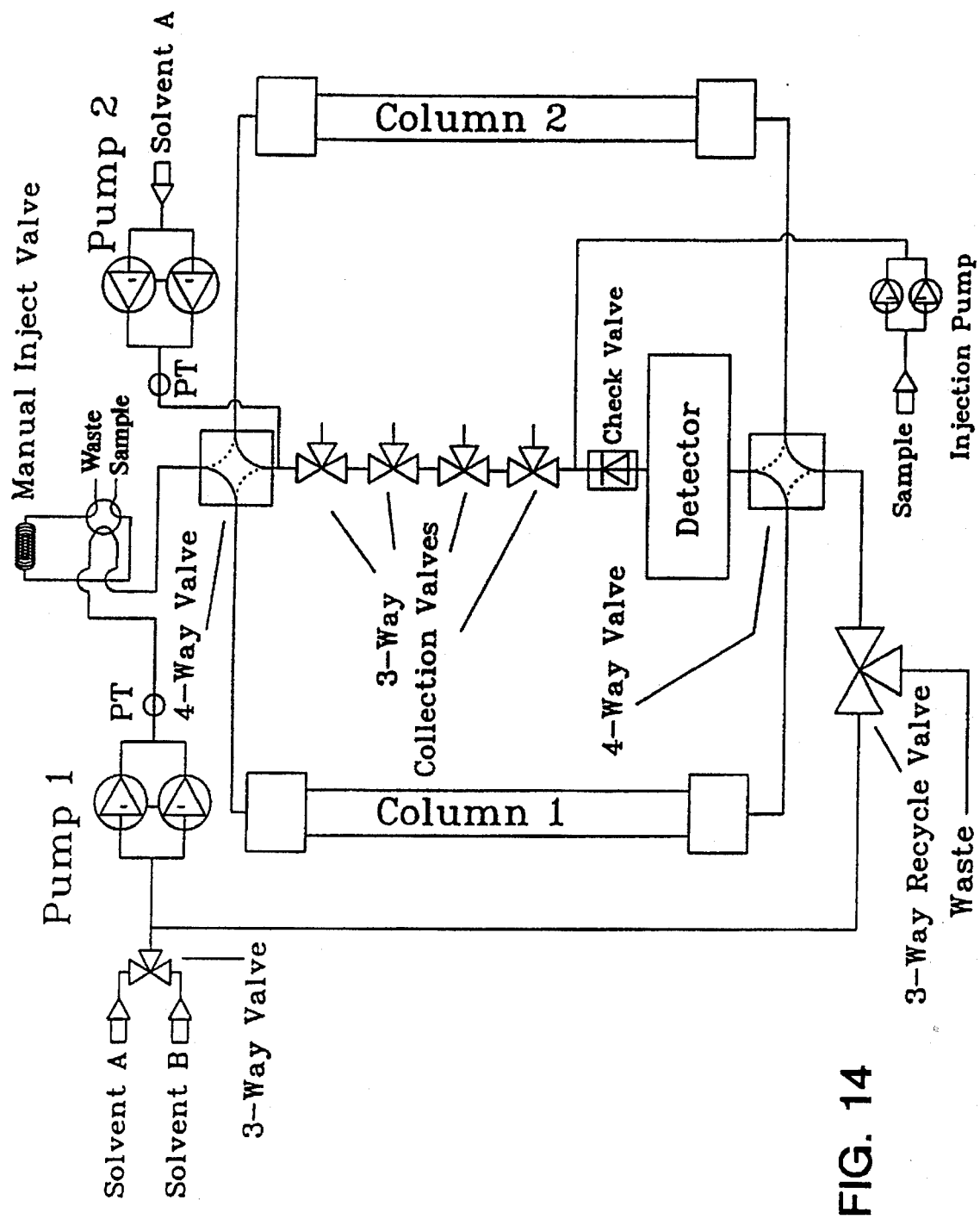
FIG. 14 is a schematic flowsheet, similar to FIG. 1, wherein the fraction collection system is a series of high pressure 3-way valves.

FIG. 14 shows another method of collecting fractions in which a series of high pressure 3-way valves are connected to the system in series.

A much larger number of fractions can be collected with any of the examples discussed above and depicted in FIGS. 12, 13 and 14 than when a 6-way sequential valve (as depicted in FIG. 2) is used. This makes the separation processes more flexible. The basic order of operation, however, is the same no matter what type of fraction collection system is used: the 4-way valves are switched to select the column order, fractions are collected on the front part of the profile, fresh sample is injected into the interior of the profile, fractions are collected on the back side of the profile.

These illustrations of fraction collection system are not intended to be exhaustive as it is possible to connect other types of fraction collection systems to the current invention. Any type of fraction collection system used in preparative chromatography can be used.

Figure 15:
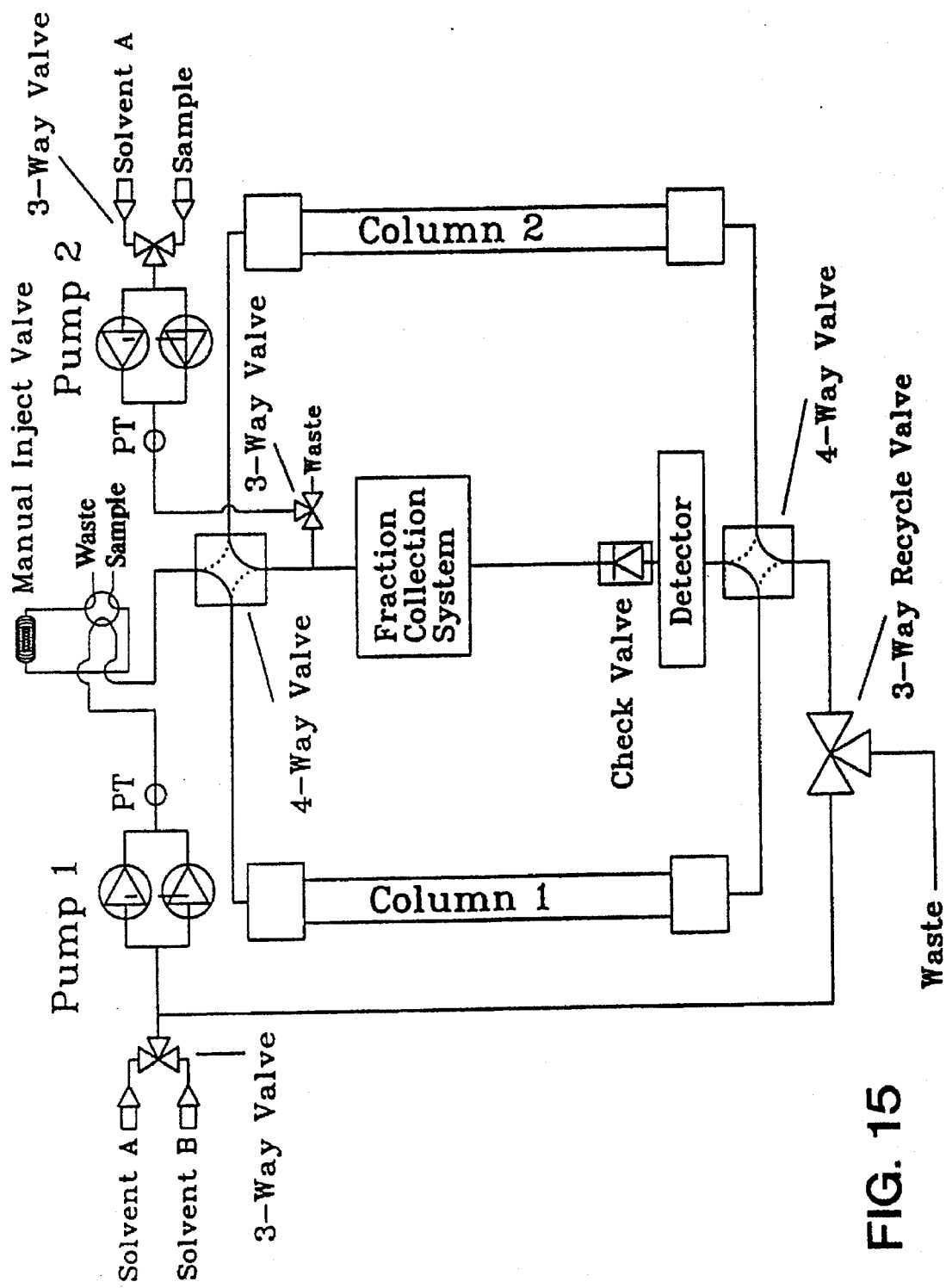
FIG. 15 is a schematic flowsheet of a modification of FIG. 1, wherein pump 2 is employed for injection of the sample, thereby eliminating the injection pump.

FIG. 15 shows a method of injecting sample using Pump 2. Using the 3-way valve, either solvent A or the sample solution can be pumped by Pump 2. Another 3-way valve is needed to purge the outlet line of Pump 2 of either solvent A or sample. Since sample can be lost during a purge, the preferred method is to use a separate injection pump as depicted in FIGS. 1 and 2.

Figure 16:
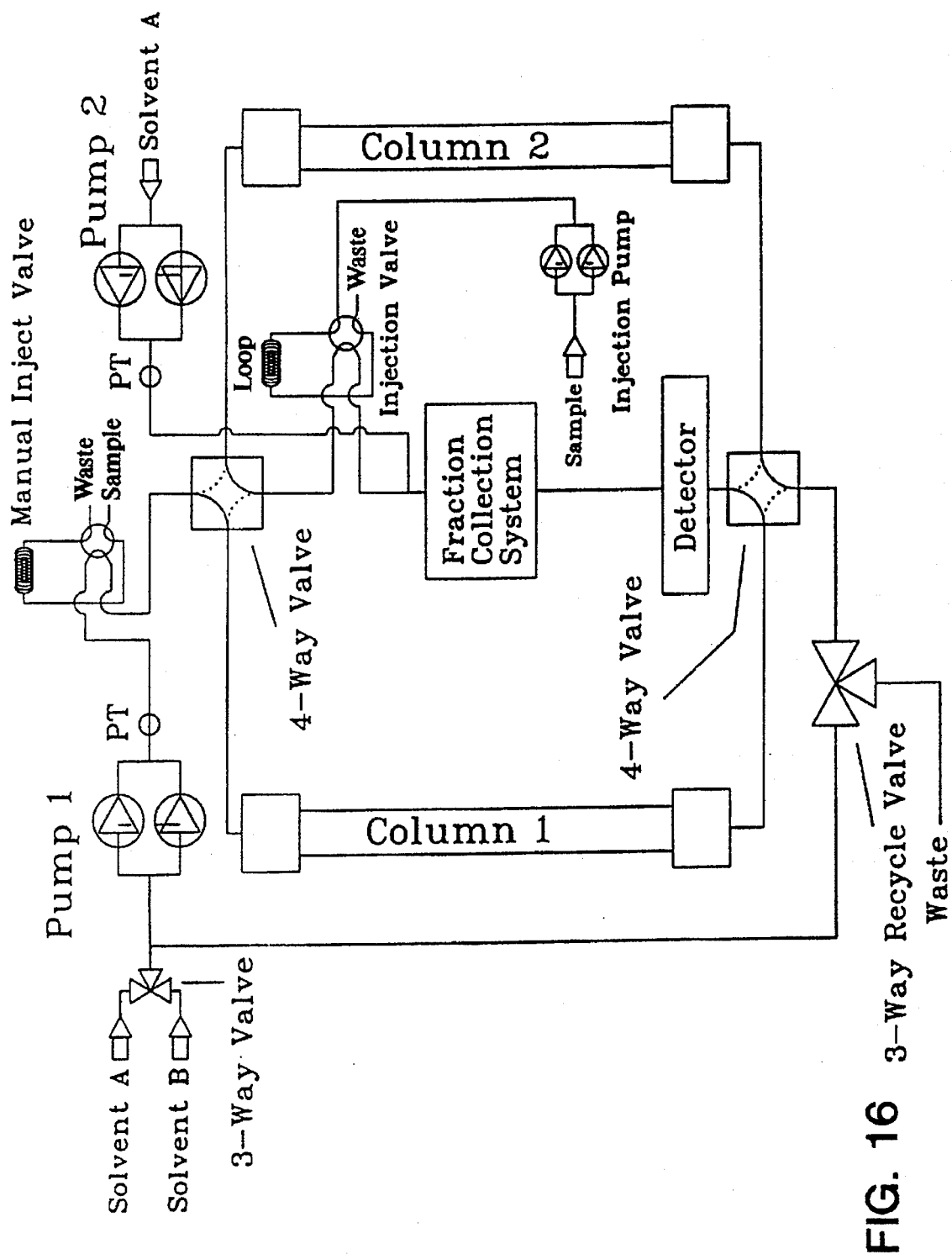
FIG. 16 is a schematic flowsheet similar to FIG. 1, but employing a calibrated injection loop.
Figure 17:
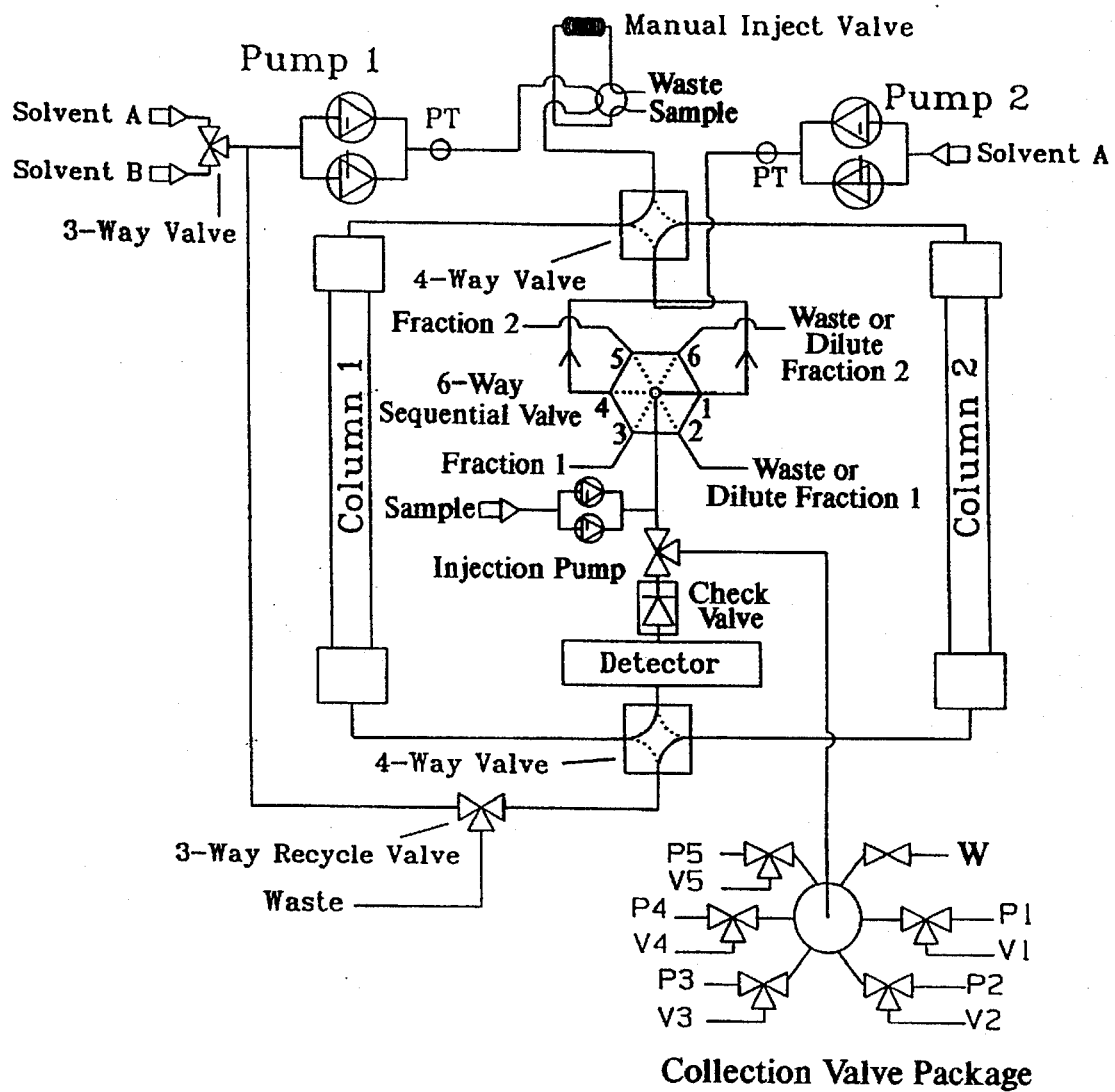
FIG. 17 is similar to FIG. 2, but employing the fraction collection system of FIG. 9.

FIG. 16 shows a method of injecting sample by using a 6-way valve and calibrated loop. This method of injection is not as flexible as that depicted in FIGS. 1 and 2, especially during methods development.

These illustrations of sample injection systems are not intended to be exhaustive as other automated injection systems are possible with the current invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

In the examples, Pump 1 and Pump 2 were ST 140 preparative HPLC pumps from EM Separations Technology. The flow rate of Pump 1 was set with the software, and the flow rate of Pump 2 was set manually with the thumb wheel on the front of the pump. The injection pump was an Eldex model B-100-S-4 metering pump. The flow rate for this pump was set manually with a micrometer. Control of Pump 1, Pump 2, and the Eldex pump was accomplished via software through an Opto 22 interface.

The two 4-way valves, the 6-way sequential valve, and their air-powered actuators were obtained from Rheodyne.

The two 3-way valves were obtained from Mace. All valves were air actuated and were controlled via software through the Opto 22 interface.

The detector was obtained from Knauer. It was a variable wavelength UV HPLC detector equipped with a high pressure flow cell.

Proprietary TurboPrep® software from EM Separations Technology was used to control all pumps and valves. The software ran on a 486 computer from Dell Computer Corporation.

The computer was connected to the system by way of an interface from Opto 22.

In all the examples, the following conditions were used. The two columns were annular expansion columns from EM Separations Technology. The dimensions of the columns were 50 mm diameter×200 mm in length. Each column was packed with approximately 244 g of RP Select B, particle size 12 μm. RP Select B is a C8 octane phase bonded to silica and is a product of E. Merck, Darmstadt, Germany.

The mobile phase was methanol:water 80:20. Both the methanol and the water were HPLC grade and were obtained from EM Science. The nominal flow rate for Pump 1 was 70 mL/min. When used, the nominal flow rate for Pump 2 was 65 mL/min.

The mixture undergoing separation was a solution of methyl and propyl p-hydroxybenzoates. The methyl and propyl p-hydroxybenzoates were obtained from Aldrich. The sample solution was made by dissolving 30 mg/mL each of methyl and propyl p-hydroxybenzoate in methanol:water 80:20. The methyl p-hydroxybenzoate is less retained and eluted first; the propyl p-hydroxybenzoate eluted second.

The flow rate of the Eldex injection pump was set at 20 mL/min. Each injection occurred for 1.0 minute giving an injection volume of 20 mL. Thus 600 mg each of methyl and propyl p-hydroxybenzoate were injected each time.

EXAMPLE 1

The preferred embodiment shown in FIG. 2 was used in this example.

In this example Pump 1 was turned off during injection to maximize the separation. Also in order to increase throughput, Pump 2 was turned on during the collection of fraction 2 and its succeeding waste step.

Figure 3:
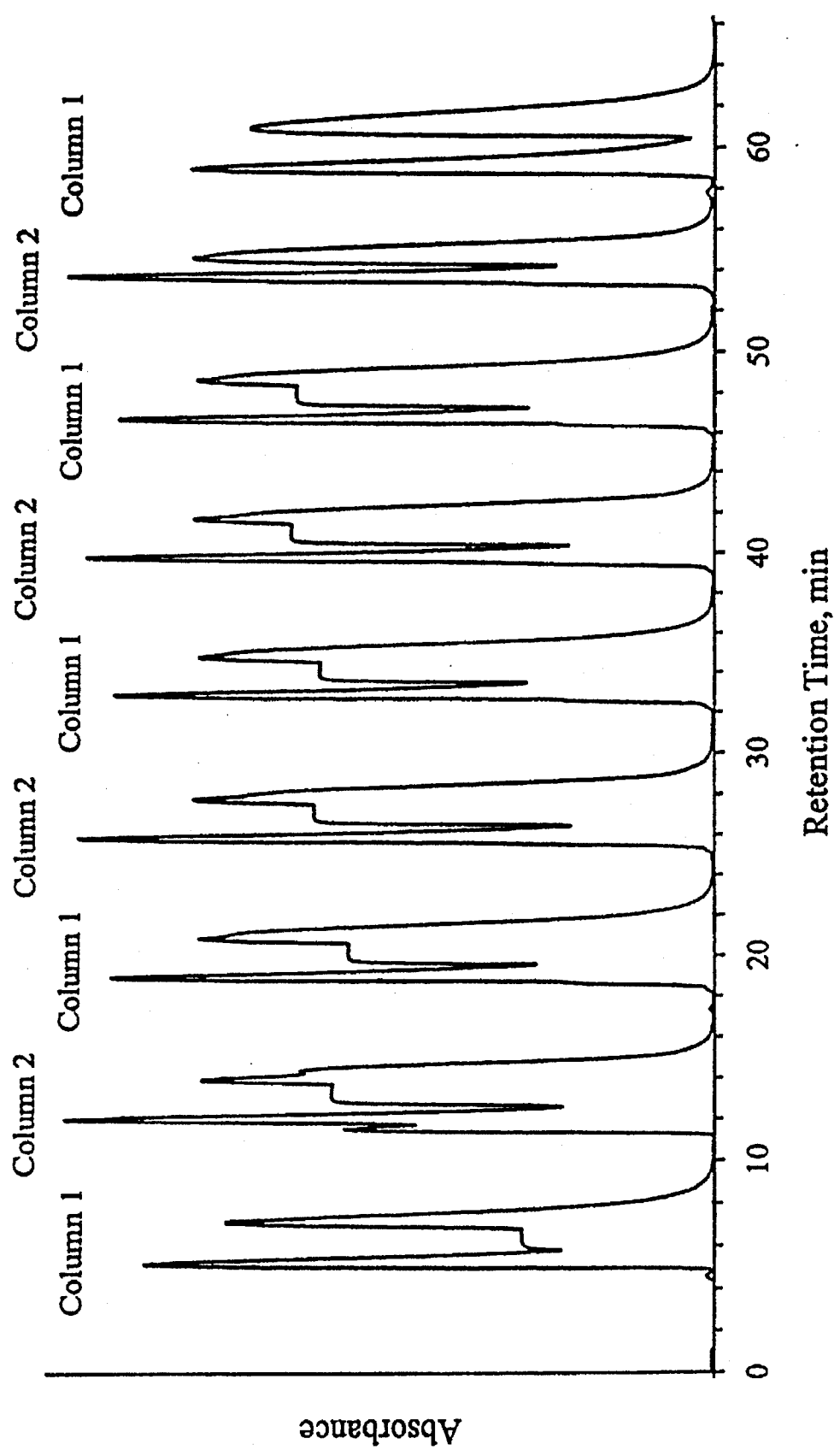
FIG. 3 is a chromatogram of Example 1.

FIG. 3 shows a chromatogram that illustrates all of the stages of the process. The end of the first 20 mL injection occurred at 0 minutes. The second injection began at about 5.8 minutes; subsequent injections occurred thereafter at 6.95 minute intervals. The flat part in the middle of the profiles is due to the shut-off of Pump 1 during injection: flow ceased through the detector resulting in a constant signal from the detector.

Decreasing the time to inject the same amount of sample would increase throughput. This could be done by increasing the flow rate of the injection pump and/or increasing the concentration of the sample solution. If the time interval could be reduced enough, Pump 1 could be left on during injection, thus maximizing throughput.

In FIG. 3, methyl p-hydroxybenzoate was collected from the front part of each profile and propyl p-hydroxybenzoate was collected from the back part. By the third cycle, steady state had been reached: from cycle 3 through cycle 7, 600 mg each of methyl and propyl p-hydroxybenzoate were injected and collected each cycle. During cycle 8 no sample was injected or collected. On cycle 9, baseline separation was obtained, permitting collection of each component in pure form.

Thus there are three stages in the exemplified process.

1. Early cycles when the system is evolving toward steady state. During these cycles, the same amount of sample is injected each time (in this case, 600 mg each of methyl and propyl p-hydroxybenzoate). However, varying amounts of each product are collected.
2. Steady state. The profiles of each steady state cycle are identical because the same amount of material is being injected and collected. The location of each event relative to the profile is the same in each cycle. The system can run indefinitely under steady state conditions.
3. Ending cycles. Injection ceases and the remaining product still in the system is collected as in ordinary preparative HPLC.

Figure 4:
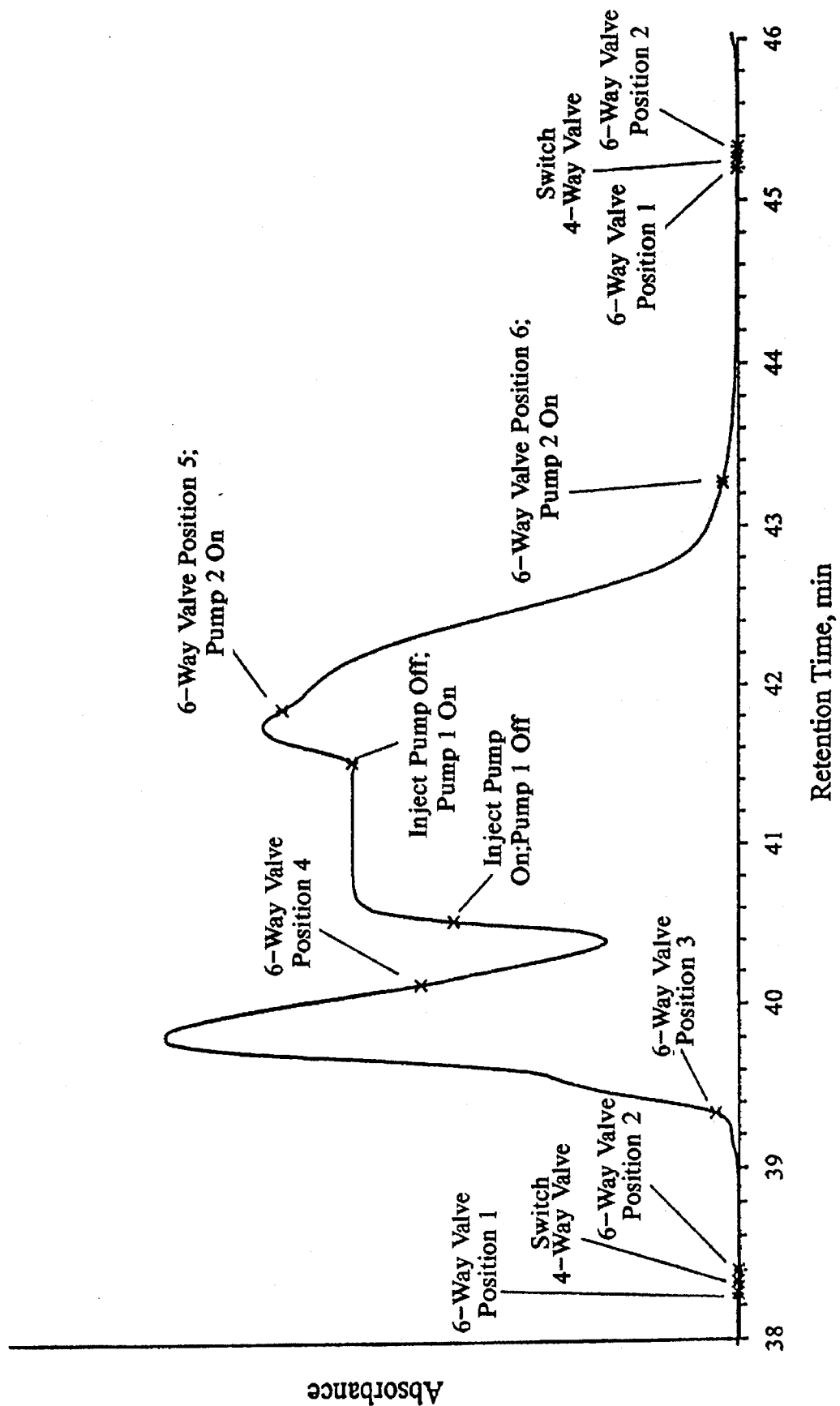
FIG. 4 is a graph of cycle 6 of Example 1.

FIG. 4 shows cycle 6, in which steady state has been achieved, in more detail.

The 4-way valves were switched at 38.30 minutes to direct the chromatographic flow from column 1 to column 2.

At 38.40 minutes, the 6-way valve was rotated to position 2, diverting the stream to waste in anticipation of the approaching profile.

At 39.33 minutes, the software having detected an ascending slope of 10% of maximum detector signal per second, the 6-way valve was rotated to position 3, collecting fraction 1 (methyl p-hydroxybenzoate).

At 40.15 minutes, the 6-way valve was rotated to position 4, ceasing collection of fraction 1 and sending the front part of the profile on to column 1. The 3-way recycle valve was set to recycle the mobile phase to the inlet of Pump 1.

At 40.55 minutes, the injection pump was turned on, and Pump 1 was shut off.

At 41.55 minutes, the injection pump was turned off, and Pump 1 was turned on.

At 41.85 minutes, the 6-way valve was rotated to position 5, collecting fraction 2 (propyl p-hydroxybenzoate); Pump 2 was turned on, preventing the stalling of the profile.

At 43.30 minutes, the 6-way valve was rotated to position 6, diverting the stream to waste. Pump 2 remained on.

At 45.20 minutes, the 6-way valve was rotated to position 1, and Pump 2 was shut off.

At 45.25 minutes, the 4-way valves were switched to direct the chromatographic flow from column 2 to column 1, thus beginning cycle 7.

The cycle time for this separation was 6.95 minutes, as can be verified by comparing the 4-way switching times of cycles 6 and 7: 45.25 min −38.30 min=6.95 min. A similar comparison between cycles of all other events also reveal a cycle time of 6.95 min. The cycle time had been determined previously and beginning in cycle 2 was imposed as timed events on all events. Thus, steady state was reached quickly by the third cycle.

Fractions 1 (methyl p-hydroxybenzoate) and 2 (propyl p-hydroxybenzoate) were analyzed by analytical HPLC using an Hitachi L-6000 pump. The mobile phase of methanol:water 60:40, and the flow rate was 2.0 mL/min. The column, having dimensions 4 mm ID×125 mm, was packing with Merck LiChrospher RP18 (12 μm particle size). A Rheodyne 6-way valve (model 700L) equipped with a 20 μL loop was used as the injection valve. The detector was a variable UV wavelength detector from Knauer. The wavelength was set at 280 nm for analysis of fraction 1; 275 nm, for analysis of fraction 2.

The results are summarized in Table 1. Fraction 1 is very pure in methyl p-hydroxybenzoate with 99.9 area percent. Fraction 2 is slightly less pure in propyl p-hydroxybenzoate with 98.7 area percent. If higher purity were required of fraction 2, less propyl and methyl p-hydroxybenzoate could be collected each cycle, with a correspondingly smaller injection of sample. As always in chromatography, the trade-off is between purity and throughout.

TABLE 1

Purity of the Fractions Expressed as Area Percents

| Fraction | methyl p-hydroxybenzoate | propyl p-hydroxybenzoate | Other |
| --- | --- | --- | --- |
| 1 | 99.9% | <0.1% | <0.1% |
| 2 | 1.3% | 98.7% | <0.1% |

EXAMPLE 2

The preferred embodiment shown in FIG. 2 was used in this example.

In this example Pump 1 was turned off during injection to maximize the separation. However, Pump 2 was not turned on during the collection of fraction 2 and its succeeding waste step. This example shows that the separation can be carried out with only one mobile phase pump (Pump 1), but at the cost of a longer cycle time and lower throughput.

Figure 5:
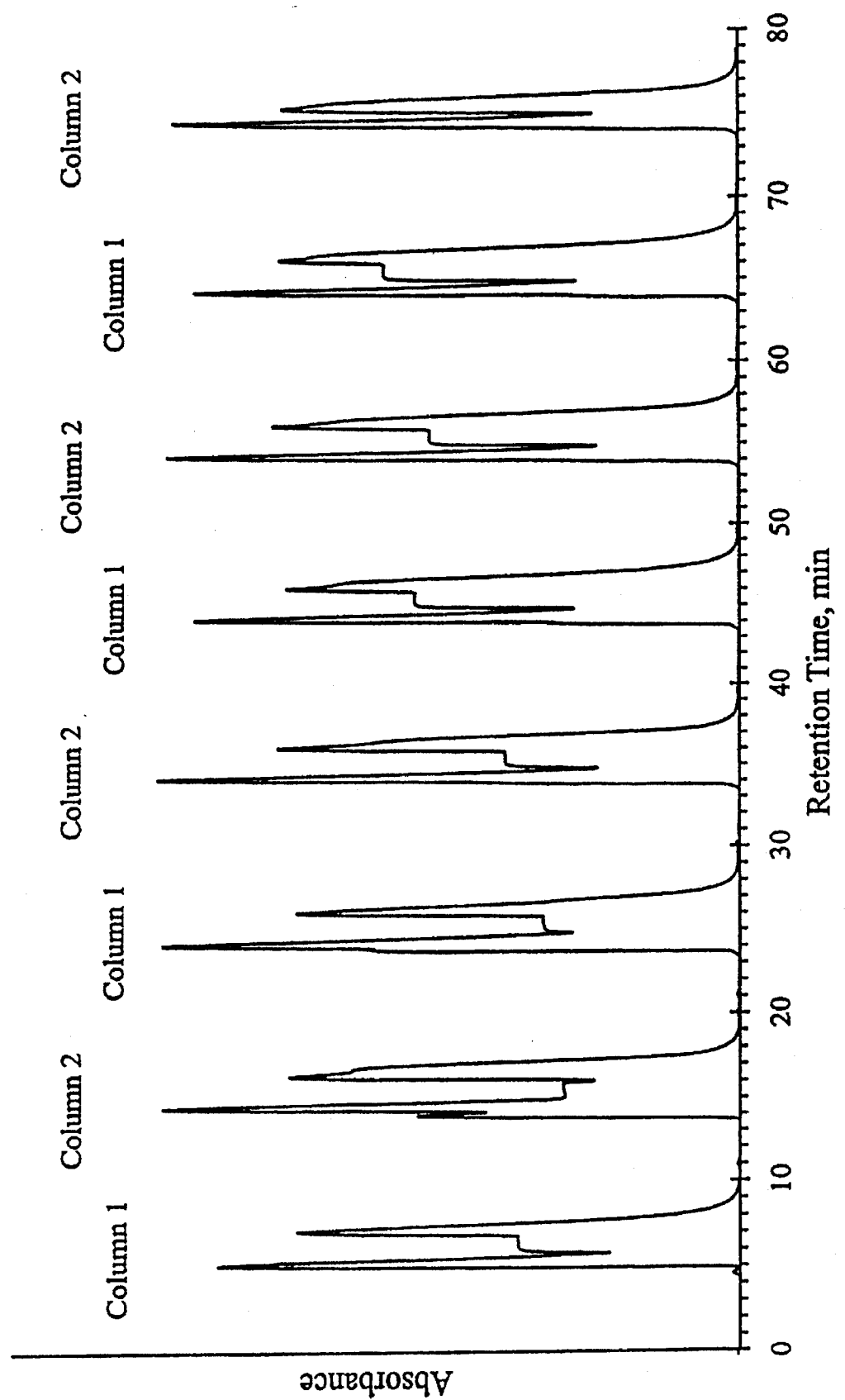
FIG. 5 is a chromatogram of Example 2.

FIG. 5 shows a chromatogram which illustrates this example. As with Example 1, the end of the first 20 mL injection occurred at 0 minutes, and the second injection began at about 5.8 minutes. Beginning with cycle 2, specific times were not imposed on any of the events except for the switching of the 4-way valves and the rotation of the 6-way valve to position 2. Both of these events occurred every 10.1 minutes beginning with the second cycle.

The other events, beginning with the second cycle, were triggered by the detection of the profile's initial increase in slope. When an ascending slope of 10% of maximum detector signal per second was detected by the software, the 6-way valve was rotated to position 3, collecting fraction 1 (methyl p-hydroxybenzoate). This event is called the triggering event. The other events occur at precise time intervals relative to each other, but do not occur at any predetermined times. Their absolute times of occurrence depend on the time of the triggering event. The correct intervals between these events were determined previously by experiment.

- At 0.8 min after the triggering event, the 6-way valve was rotated to position 4, ceasing collection of fraction 1 and sending the uncollected part of the profile on to column 1. The 3-way recycle valve was set to recycle the mobile phase to the inlet of Pump 1.
- At 1.2 min after the triggering event, the injection pump was turned on, and Pump 1 was turned off.
- At 2.2 min after the triggering event, the injection pump was turned off, and Pump 1 was turned on.
- At 2.5 min after the triggering event, the 6-way valve was rotated to position 5, collecting fraction 2 (propyl p-hydroxybenzoate); Pump 2 was not turned on.
- At 3.95 min after the triggering event, the 6-way valve was rotated to position 6, diverting the stream to waste. Pump 2 was not turned on.
- At 5.85 min after the triggering event, the 6-way valve was rotated to position 1.

As with Example 1 the flat part in the middle of the profiles is due to the shut off of Pump 1 during injection:

flow ceased through the detector resulting in a constant signal from the detector. By the fifth cycle steady state appears to have been reached. In cycle 8 no sample was injected or collected allowing the collection of each component in pure form in cycle 9 (not shown) as in Example 1.

Since no specific time was imposed on the events summarized above, the system reached steady state in cycle 5—two cycles more than was required in Example 1. Table 2 shows the time intervals between the same events in succeeding cycles. Note that beginning with cycle 4, these time intervals equaled about 10.07 minutes. We can conclude from this result that the true cycle time is near 10.07 minutes. Thus, this procedure (allowing correctly spaced events to be triggered by the detection of the beginning of the profile) is useful in determining the cycle time during methods development.

TABLE 2

| Event | Time Intervals Between Events from Cycle to Cycle, minutes | | | | | |
| --- | --- | --- | --- | --- | --- | --- |
| | Cycle 2 | Cycle 3 | Cycle 4 | Cycle 5 | Cycle 6 | Cycle 7 |
| 6-way Valve Position 3 | 8.80 | 9.94 | 10.06 | 10.07 | 10.07 | 10.06 |
| 6-way Valve Position 4 | 9.33 | 9.94 | 10.06 | 10.07 | 10.07 | 10.06 |
| Injection Pump On | 9.13 | 9.94 | 10.06 | 10.07 | 10.07 | 10.06 |
| Injection Pump Off | 9.13 | 10.06 | 10.07 | 10.07 | 10.07 | 10.06 |
| 6-Way Valve Position 5 | 9.00 | 10.00 | 10.07 | 10.00 | 10.06 | 10.07 |
| 6-Way Valve Position 6 | 9.14 | 10.00 | 10.00 | 10.06 | 10.07 | 10.07 |
| 6-Way Valve Position 1 | 9.60 | 10.00 | 10.07 | 10.00 | 10.13 | 10.07 |

EXAMPLE 3

The preferred embodiment shown in FIG. 2 was used in this example.

In this example, Pump 1 is not turned off during injection. This example is an extreme case in that the time interval during which the injection pump is turned on is a significant fraction of the entire profile. Thus resolution of the component compounds is less than in Examples 1 and 2. In order to maintain steady state, the purity of the two fractions is less than in Examples 1 and 2. The time needed to inject the same amount (in this case, 600 mg each of methyl and propyl p-hydroxybenzoate) can be reduced by increasing the flow rate of the injection pump and/or increasing the concentration of the sample solution. Either of these or a combination would improve the purity of the fractions without decreasing the throughput. Of course, the separation could also be improved by injecting less sample at the same injection pump flow rate. However, this would result in reduced throughput.

Figure 6:
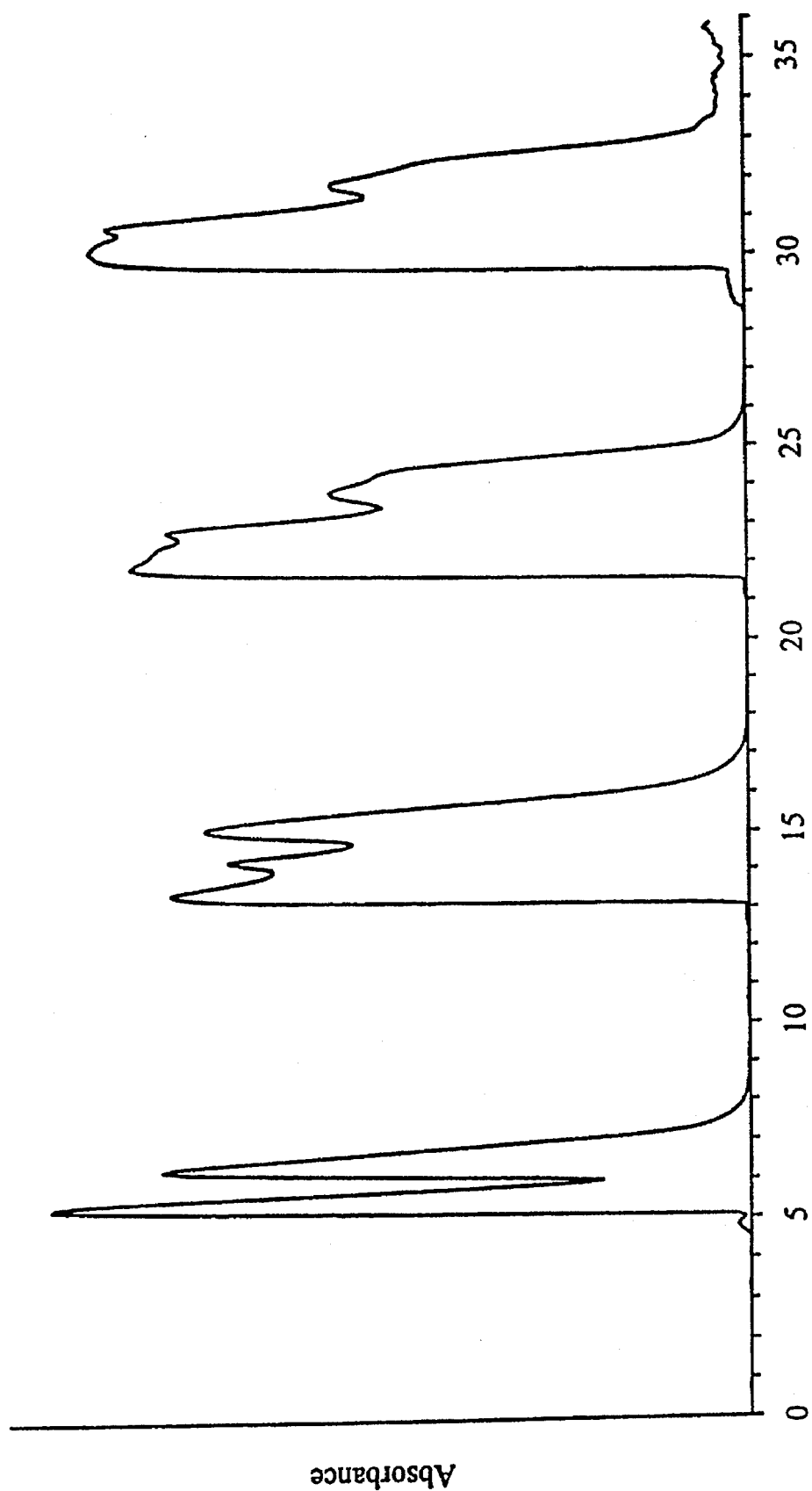
FIG. 6 is a chromatogram of Example 3.
Figure 7:
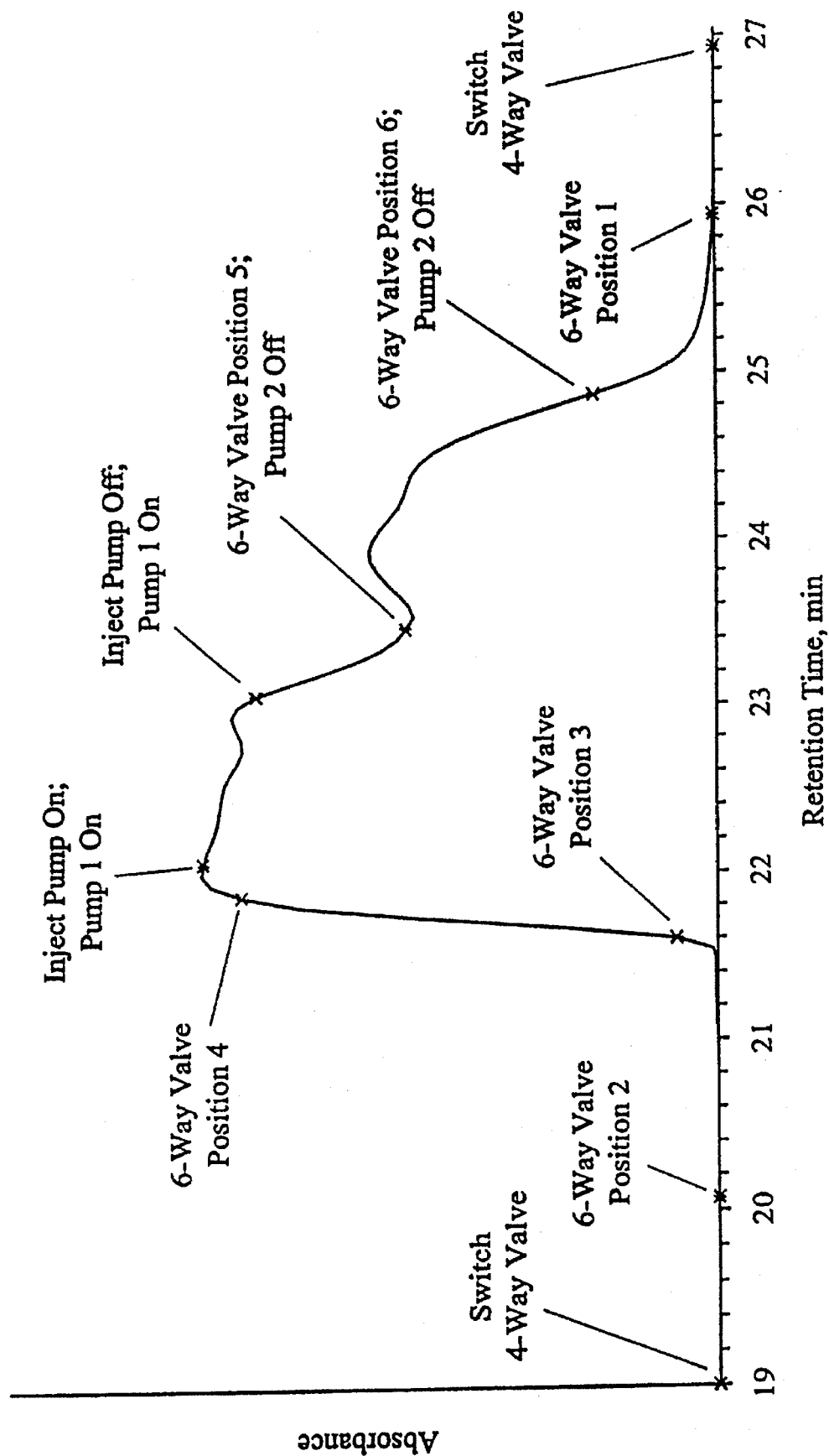
FIG. 7 is a graph of cycle 3 of Example 3.

FIG. 6 shows a partial chromatogram of this example, and FIG. 7 shows cycle 3 in more detail. Note that because Pump 1 is never turned off, there is no flat region in the middle of the profiles as in Examples 1 and 2. However, it is also obvious that, beginning with cycle 2, the resolution is worse than in Examples 1 and 2. The resolution could be improved by using any of the techniques discussed above.

Also, in this example, Pump 2 does not turn on during the collection of fraction 2 and during its subsequent waste step. The throughput could be significantly improved by using Pump 2, as is shown in the next Example.

EXAMPLE 4

In this example, as in Example 3, Pump 1 is not turned off during injection. However, Pump 2 is turned on during the collection of fraction 2 and its subsequent waste step.

Figure 8:
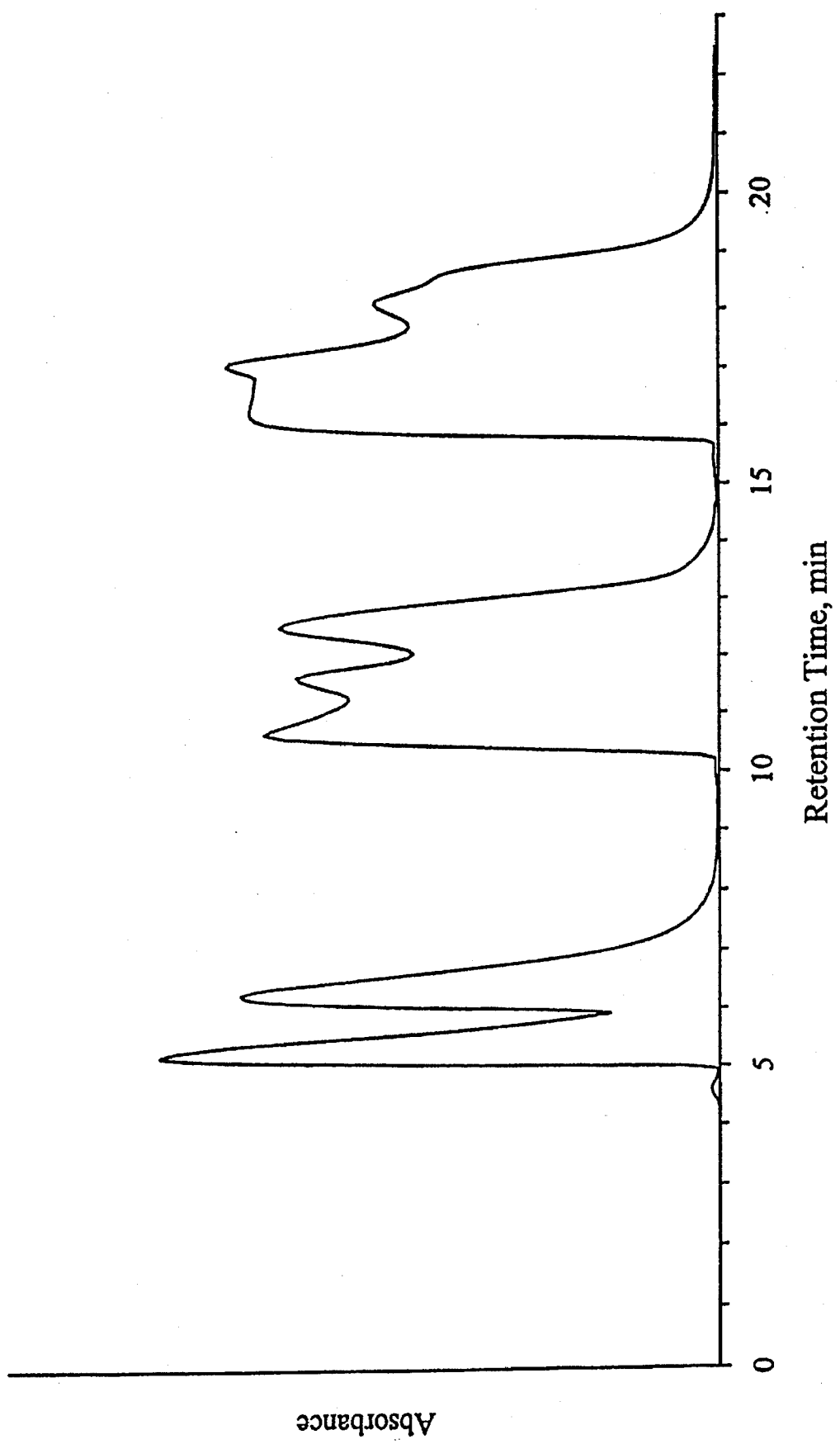
FIG. 8 is a chromatograph of Example 4.

The first 3 cycles are shown in FIG. 8. Their profiles are virtually identical to those of Example 3 except they are closer together. Pump 2, by turning on during the collection of fraction 2 and its subsequent waste step, prevented the profile from stalling.

EXAMPLE 5

Figure 9:
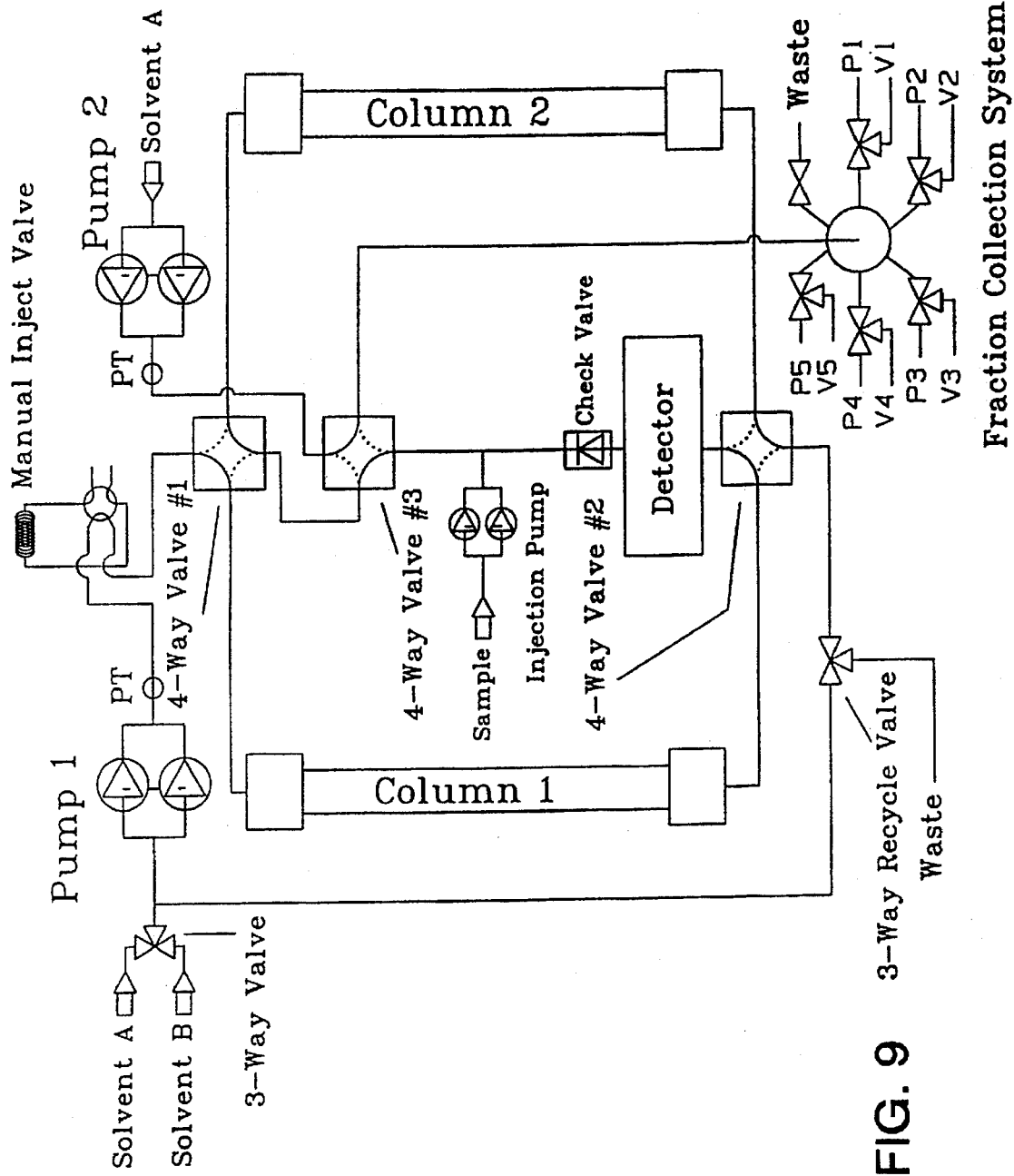
FIG. 9 is a schematic flowsheet of the system used in Example 5, having a third 4-way valve instead of the 6-way sequential valve in FIG. 2, and also provided with a more sophisticated fraction collection system.

FIG. 9 shows a schematic diagram of the system used in this example. The 6-way sequential valve in FIG. 2 has been replaced by 4-way valve #3 that leads to an array of fraction collection valves. With this design, any collection valve can be chosen in any order. It is therefore, more flexible than the design shown in FIG. 2 in which one is constrained to choose collection lines in a specific order. In its default position, 4-way valve #3 by-passes the collection valve array and communicates directly with 4-way valve #1.

Note in FIG. 9 that 4-way valve #3 connects Pump 2 to the system. During the collection of fractions that occur after in the sample injection step, Pump 2 can be turned on to prevent stalling of the chromatographic profile. When 4-way valve #3 has been switched back to the default position, Pump 2 can be turned on to wash sample from the common line leading to the fraction collection array, thus avoiding contamination of fractions.

Figure 10:
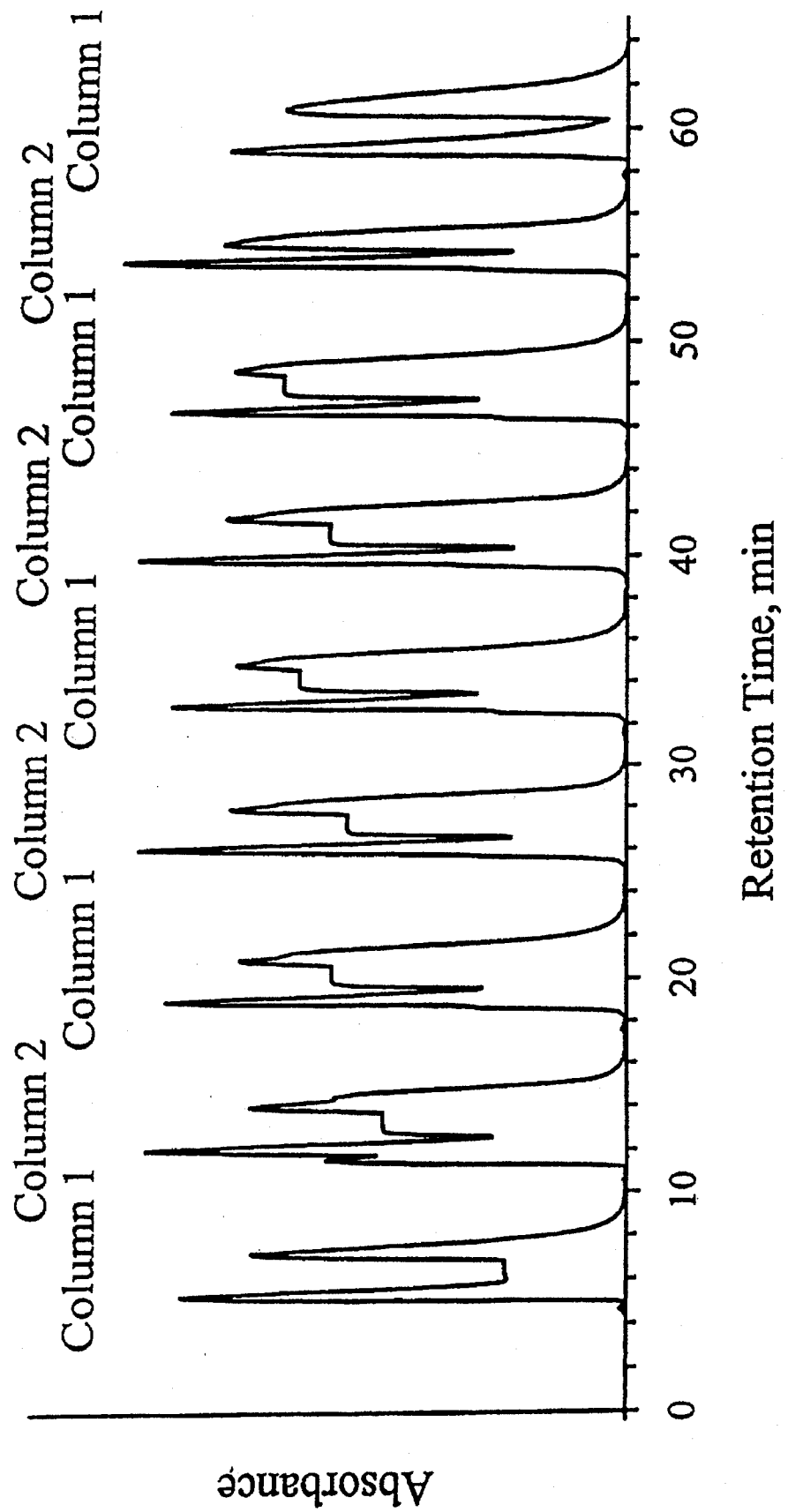
FIG. 10 is a chromatogram of Example 5.

FIG. 10 shows a chromatogram that illustrates the use of this design in the separation process. Note that is very similar to FIG. 3, the chromatogram for Example 1. This is to be expected since the separation process is the same: we are merely using a different method of collecting the fractions in this Example 5. As with Example 1, the cycle time for the current example was 6.95 minutes.

Figure 11:
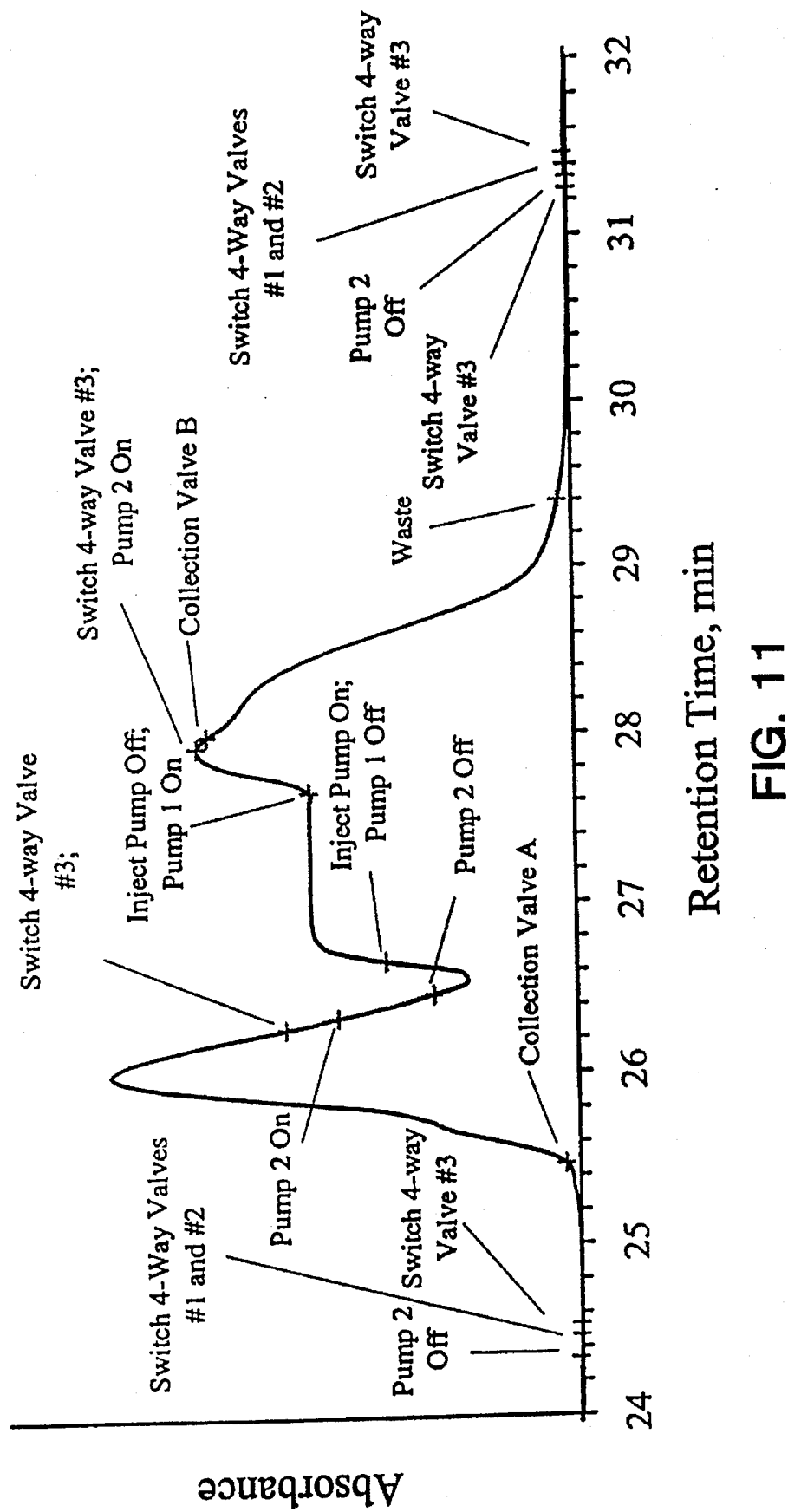
FIG. 11 is a graph of cycle 4 of Example 5.

FIG. 11 shows cycle 4, in which steady state has been achieved, in more detail.

At 24.35 minutes, 4-way valve #3 was switched, directing the flow to column 2. Pump 2 remained on to wash the common collection line.

At 24.37 minutes, Pump 2 was turned off.

At 24.40 minutes, 4-way valves #1 and #2 were switched, directing the output from Pump 1 to column 2 and the output of column 2 to column 1.

At 24.50 minutes, 4-way valve #3 was switched, diverting the stream to waste (whose valve is normally open) in anticipation of the approaching chromatographic profile.

At 25.47 minutes, the software having detected an ascending slope of 10% of maximum detector signal per second, collection valve 1 was opened to collect from 1.

At 26.25 minutes, 4-way valve #3 was switched, ceasing collection of fraction 1 and sending the front part of the profile on to column 1. The 3-way recycle valve was set to recycle the mobile phase to the inlet of Pump 1.

At 26.30 minutes, the waste valve in the 6-valve collection array was opened.

At 26.40 minutes, Pump 2 was turned on to wash the common fraction collection line to avoid cross contamination.

At 26.60 minutes, Pump 2 was turned off.

At 26.65 minutes, the injection pump was turned on, and Pump 1 was shut off, and the recycle valve was set to waste.

At 27.65 minutes, the injection pump was turned off, and Pump 1 was turned on, and the recycle valve was set to recycle mobile phase to the inlet of Pump 1.

At 27.90 minutes, collection valve #2 was opened in anticipation of collection fraction 2.

At 27.95 minutes, 4-way valve #3 was switched resulting in the collection of fraction 2. Simultaneously, Pump 2 was turned on, preventing the stalling of the chromatographic profile.

At 29.40 minutes, the waste valve in the 6-valve collection array was opened diverting the stream to waste. Pump 2 remained on.

At 31.30 minutes, 4-way valve #3 was switched directing the flow to column 1. Pump 2 remained on to wash to common collection line.

At 31.32 minutes, Pump 2 was turned off.

At 31.35 minutes, 4-way valves #1 and #2 were switched directing the output from Pump 1 to column 1 and the output of column 1 to column 2.

The method of collecting fractions in the current example requires more steps than that used in Example 1. To collect a fraction, 4-way valve #3 must be opened, and the collection valves of interest must be opened. Also, the common collection line must be washed between fractions to prevent cross contamination. However, since the collection valves can be opened in any order and since more collection valves can easily be added, the fraction collection method used in the current example is more flexible than that used in Example 1–4.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. A preparative chromatographic cyclical process comprising, at substantially steady state:

(a) establishing a figure-of-eight circulating chromatographic profile between two chromatographic columns with the provision that said chromatographic profile never passes through a pump;

(b) discontinuously and periodically injecting a sample comprising at least two components, into the interior of said circulating profile;

(c) collecting, discontinuously and periodically, at least two enriched fractions from said circulating profile; and (d) through a first solvent pump, pumping solvent, as a mobile phase, substantially continuously into one of said chromatographic columns during a single cycle.

2. A process according to claim 1, further comprising pumping solvent through a second solvent pump into a column so as to prevent stalling of the chromatographic profile during collection of fractions occurring later in a cycle than said injecting of sample.

3. A process according to claim 2, further comprising shutting off said first solvent pump during said injecting of sample.

4. A chromatographic process according to claim 3, further comprising periodically terminating pumping said mobile phase while immediately sending a pulse of solvent into one of said columns so as to elute fractions more quickly that occur later in a cycle than said injecting, said pulse of solvent being stronger than the mobile phase solvent.

5. A chromatographic process according to claim 2, further comprising periodically terminating pumping said mobile phase while immediately sending a pulse of solvent into one of said columns so as to elute fractions more quickly that occur later in a cycle than said injecting, said pulse of solvent being stronger than the mobile phase solvent.

6. A process according to claim 1, further comprising shutting off said first solvent pump during said injecting of sample.

7. A chromatographic process according to claim 6, further comprising periodically terminating pumping said mobile phase while immediately sending a pulse of solvent into one of said columns so as to elute fractions more quickly that occur later in a cycle than said injecting, said pulse of solvent being stronger than the mobile phase solvent.

8. A chromatographic process according to claim 1, further comprising periodically terminating pumping said mobile phase while immediately sending a pulse of solvent into one of said columns so as to elute fractions more quickly that occur later in a cycle than said injecting, said pulse of solvent being stronger than said mobile phase solvent, and then resuming pumping the mobile phase through the said pump.

9. A process according to claim 1, wherein said figure-of-eight chromatographic profile circulates continuously.

* * * * *